United States Patent [19]

Yoshikumi et al.

[11] 4,140,578

[45] Feb. 20, 1979

[54] METHOD OF PRODUCING POLYSACCHARIDES

[75] Inventors: Chikao Yoshikumi, Kunitachi; Toshihiko Wada, Mibu; Masahiko Fujii, Iwaka; Hiromitsu Makita, Iwaki; Kinzaburo Suzuki, Iwaki; Akio Shinmyo, Mibu; Haruhisa Hayashi, Tokyo, all of Japan

[73] Assignee: Kureha Kagaku Kogyo Kabushiki Kaisha, Tokyo, Japan

[21] Appl. No.: 817,226

[22] Filed: Jul. 20, 1977

[30] Foreign Application Priority Data

Jul. 22, 1976 [JP] Japan .................................. 51-87503

[51] Int. Cl.$^2$ ........................ C12D 13/04; C08B 37/00
[52] U.S. Cl. ..................................... 195/31 P; 195/81; 536/1
[58] Field of Search ..................... 195/31 P, 81; 536/1, 536/18; 424/181

[56] References Cited

U.S. PATENT DOCUMENTS

| | | | |
|---|---|---|---|
| 3,301,848 | 1/1967 | Halleck | 536/1 |
| 3,759,896 | 9/1973 | Komatsu et al. | 195/31 P |
| 3,810,819 | 5/1974 | Okamoto et al. | 195/4 |
| 4,051,314 | 9/1977 | Ohtsuka et al. | 195/31 P |

FOREIGN PATENT DOCUMENTS

1331513  9/1973  United Kingdom .................. 195/31 P

*Primary Examiner*—Thomas G. Wiseman
*Attorney, Agent, or Firm*—Lane, Aitken & Ziems

[57] ABSTRACT

A fungus belonging to genus Coriolus of the class Basidiomycetes is subjected to submerged culture in a liquid medium and the obtained culture is dried and extracted with an aqueous solvent, and then the substances with molecular weights of less than 5,000 are eliminated from the extract solution, whereby a polysaccharide having anti-cancer and other pharmacodynamic effects is obtained in a high yield.

5 Claims, No Drawings

METHOD OF PRODUCING POLYSACCHARIDES

FIELD OF THE INVENTION

This invention relates to a method of producing a polysaccharide useful for preparation of medicaments, particularly an anti-cancer medicine, from the cultured broth obtained from submerged culture of a fungus belonging to genus Coriolus of the class Basidiomycetes.

BACKGROUND OF THE INVENTION

It is known that a polysaccharide having anti-tumor activity can be obtained from a broth which has undergone culture of a fungus of the class Basidiomycetes with an aqueous liquid medium. It is also an established fact that when a fungus of the class Basidiomycetes is subjected to submerged culture with a liquid medium, the desired polysaccharide is produced not only in the mycelia but also in the medium.

Therefore, for producing a polysaccharide from such submerged culture of a fungus of the class Basidiomycetes, there has been generally employed a method in which the mycelia are crushed while keeping the used medium (cultured broth) in the form as it is or after adding water thereto, then the cultured broth is subjected to filtration or centrifugal separation to remove the mycelial residue therefrom, and the desired polysaccharide is collected from the resulting liquor portion.

Although such method is certainly appraised as rational and practical, it still involves some serious problems. For instance, where the submerged culture product is immediately separated into the mycelia and the liquor, such separation can not be accomplished efficiently due to the elevated viscosity of the system and also due to the high water content of the mycelia. Addition of water may decrease the viscosity of the cultured broth and increase the rate of extraction into water, but the use of an excessive amount of water results in an increased time for the separation and does not decrease the water content of the mycelia.

For these reasons, improvements in the method of obtaining a desired polysaccharide from the above-mentioned submerged culture at higher efficiency and in a higher yield from the industrial viewpoint have been demanded.

SUMMARY OF THE INVENTION

The principal object of this invention is to provide a method of obtaining a polysaccharide having anti-cancer and other preferred pharmacodynamic activity from submerged culture of a fungus of the class Basidiomycetes on a commercial scale and in a high yield.

The other objects of this invention will become apparent from a consideration of the following detailed description of the invention.

The method of this invention is characterized in that a fungus belonging to Coriolus of the class Basidiomycetes if first subjected to submerged culture with an aqueous liquid medium and the obtained cultured broth is dried at a temperature of 60° C.–150° C. and extracted with an aqueous solvent, and then the thus obtained extract solution is refined by removing therefrom the substances with molecular weights of less than 5,000. The most salient feature of the method of this invention is that the desired substance is not directly collected from the cultured broth but is obtained after once drying the cultured broth and then extracting it with an aqueous solvent.

DETAILED DESCRIPTION OF THE INVENTION

The fungi of the class Basidiomycetes used in the present invention are the ones which belong to the genus Coriolus and which include, for example, *Coriolus versicolor* (Fr.) Quél, *Coriolus consors* (Berk.) Imaz., *Coriolus hirsutus* (Fr.) Quél, *Coriolus pargamenus* (Fr.) Pat., *Coriolus pubescens* (Fr.) Quél and *Coriolus conchifer* (Schw.) Pat. The morphological features and mycological properties of these basidiomycetes are explicated in "COLOURED ILLUSTRATIONS OF FUNGI OF JAPAN" by Rokuya Imazeki and Tsuguo Hongo, Vols. I, 1974, and II, 1975. Among these basidiomycetes, those which are listed below are deposited in the Fermentation Research Institute of the Agency of Industrial Science and Technology, which is a depository organ designated by the Director-General of the Patent Office of Japan:

|  | Dep. No. | Dep. Date |
|---|---|---|
| Coriolus versicolor (Fr.) Quel | FERM-P-2414 | Dec. 25/73 |
| Coriolus consors (Berk.) Imaz. | FERM-P-988 | Jun. 24/71 |
| Coriolus hirsutus (Fr.) Quel | FERM-P-2711 | Sept. 6/74 |
| Coriolus pargamenus (Fr.) Pat. | FERM-P-2712 | Sept. 6/74 | as mentioned above are cultured by a submerged culture method. The term "submerged culture method" used herein means a method in which culture is practiced in a liquid medium under aeration and agitation, and the growth of the mycelia is effected not at the surface of the liquid medium but mostly in the deep portion of the liquid layer. Such culture is generally practiced at an aeration rate of about 0.1 to 2.0 1/1/mm (medium) and a stirring speed of about 30 to 800 r.p.m.

The medium used for the submerged culture may be of any known type of natural or snythetic media generally used in culture of microorganisms, or suitable modification of such known media. About a 3–10 day culture with such a medium is sufficient to produce the desired polysaccharide in a satisfactorily high yield.

In a submerged culture using an aqueous medium, the mycelia won't propagate at the liquid surface to form large masses as in the case of stationary culture but are formed into relatively small pellet-like or fibrous pieces owing to the shearing force produced by agitation. During this process, the polysaccharide is produced not only in the inside of the mycelia but also outside thereof, that is, in the medium as well.

In the present invention, the cultured broth obtained from the above-mentioned submerged culture of a fungus of the class Basidiomycetes is subjected to drying. This drying is accomplished usually at a temperature within the range of 60 to 150° C. The drying means may be any commonly employed type such as drum dryer, flush dryer or thinlayer evaporator.

The culture drying treatment produces the effect of greatly facilitating the ensuing extraction with an aqueous solvent as well as the collection of the polysaccharide by refining of the extract solution. It is to be noted that if the temperature of this drying treatment is lower than 60° C., there results not only a reduced drying speed but also unsatisfactory attainment of the above-stated effects. It should be noted that the desired polysaccharide has a tendency to decompose as the drying temperature rises, so that it is recommended to perform the drying treatment at a temperature not exceeding 150° C.

The culture broth which has undergone the drying treatment such as mentioned above is then extracted with an aqueous solvent by a method commonly used in extraction of fruit bodies or mycelia. The term "aqueous solvent" used herein means water or an aqueous solution containing an alkali, salt (e.g. sodium chloride, sodium acetate), polar organic solvent (e.g. methanol, ethanol) or the like, but in the present invention, extraction under heating with water or a dilute alkaline solution is most effective, and adaptation of the multiple extraction techniques by use of such extract solutions is most advantageous for industrial applications.

The extract solution thus obtained is then subjected to the treatment for refining the solution by removing therefrom substances with molecular weight of less than 5,000, thereby obtaining the desired polysaccharide. This treatment may be accomplished by using any known suitable method such as salting-out, dialysis, ultrafiltration, reverse osmosis, ion-exchange resin treatment, gel filtration or precipitation with an organic solvent. These methods may be used either singly or in combination.

Of these methods, most effective for the purpose of this invention are ultrafiltration and reverse osmosis.

After removal of the low-molecular weight components (with molecular weights of less than 5,000) from the extract solution by the above-mentioned refining treatment, the extract solution is subjected to spray drying or freeze drying and then prepared into commercial products.

The polysaccharide obtained according to the present invention in the above-described manner is a liver-brown substance with a nitrogen content of 2 to 8%, in most cases 3 to 6%, and such substance shows no express melting point and is gradually blackened and decomposed at a temperature of higher than about 120° C. The polysaccharide is soluble in water but almost insoluble in alcohol, pyridine, chloroform, benzene and hexane. Also, it is almost tasteless and odorless.

Table 1 below shows the results of various color reaction tests conducted on the polysaccharide.

Table 1

| Color reaction | Color | Results | |
|---|---|---|---|
| α-naphthol-sulfuric acid reaction (Molish's reaction) | Purple | Saccharides, | confirmed |
| Indole-sulfuric acid reaction (Disch's reaction) | Brown | Saccharides, | confirmed |
| Anthrone-sulfuric acid reaction | Greenish blue | Saccharides, | confirmed |
| Phenol-sulfuric acid reaction | Brown | Saccharides, | confirmed |
| Triptophane-sulfuric reaction | Purplish borwn | Saccharides, | confirmed |
| Lowry-Folin process | Blue | Peptide bonds, | confirmed |
| Ninhydrin reaction after hydrochloric acid hydrolysis | Purplish blue | α-amino acids, | confirmed |

The test results given in the above table indicate that the obtained product is a nitrogen-containing polysaccharide. Its molecular weight, as measured by the ultracentrifugal method, was within the range of 5,000 to 300,000 and the average molecular weight was 10,000 to 100,000. The values obtained from other measuring methods, such as fractionation with an ultrafiltration membrane, were all within the range of 10,000 to 100,000. Therefore, it is a highly reliable estimate to assign an average molecular weight within the range of 10,000 to 100,000.

The nitrogen-containing polysaccharide provided according to the present invention demonstrated a very excellent antitumor activity in mice not only in intraperitoneal administration but also in oral administration. This signifies excellent availability of the polysaccharide as an oral anti-cancer medicine. In fact, such effect has been ascertained by many and various experiments. In addition to the oral anti-tumor effect, the product also exhibited a high activity in restoring the suppressed immunity of the host. That is, the polysaccharide was useful not only for preventing, the unfavorable side effects in chemotherapy of cancer and increasing sensitivity in radiotherapy but also for preventing a decline in immunity or physical strength of the patient resulting from a surgical operation or blood transfusion and for controlling or preventing infection by virus or bacteria which becomes liable with decline of the physical strength or immunity of the patient. Oral administration of the product also produced an excellent effect in improving the liver function, promoting the appetite, remedying intestinal disorders and promoting urination. It was also useful for the treatment of leprosy.

In the following example, all percents (%) are by weight unless otherwise noted.

EXAMPLE 1,600 liters of a medium composed of 10% of glucose, 1.5 % of yeast extract, 0.1 % of $KH_2PO_4$ and 0.1 % of $MgSO_4 \cdot 7H_2O$ was fed into a 2-m$^3$ vertical fermentator and this medium was inoculated with 20 liters of fungus slurry of Coriolus versicolor (Fr.) Quél FERM-P-2414 obtained from a shaking culture, followed by 7-day culture at 26° C., with an aeration rate of 0.5 1/min per litre of medium and a stirring rate of 150 r.p.m.

The thus obtained cultured broth (slurry) was divided into about 500-liter portions, and each of these portions was dried by a double-drum type drier. The surface temperature of the drum drier was adjusted such that the temperature of the surface of the cultured broth (the broth surface being attached in the form of a thin layer to the drum surface) was 65° C., 80° C., 90° C., 110° C., and 145° C., respectively, and that the water content of each dried product was less than 20 weight % (see Table 2 below).

Then, each of these dried products was added to 250 liters of hot water and extracted at 95 ± 1° C. for 3 hours, and after cooling, it was separated into the mycelial residue and the extract solution by using a screw type decanter and a separating plate type centrifugal separator. The apparent viscosity of the mixture systems and the times required for the centrifugal separation in this extraction process were as shown in Table 2.

The extract solution obtained from the above-described treatment was passed through a PM-5 membrane of a HF-Type Ultrafilter, by Amicon Co., to remove the extract components with molecular weights of less than 5,000 resulting in approximately 100 liters of the refined solution. As the concentration of this refined solution was about 1 %, it was concentrated by a concentrator to a level of concentration suited for the ensuing treatment of spray drying. As the refined solution would gel to make the treatment difficult to carry on if the solution is concentrated beyond a certain degree, the limit value of concentration under which no gelation takes place is shown as critical concentration in Table 2.

The time required for spray drying the above-mentioned concentrated solutions and the yields of the obtained polysaccharide are also shown in Table 2.

For the sake of comparison (Comparative Examples), cultured broths obtained from the same procedure as described above was treated similarly to the above-described embodiment after drying at 45° C., 160° C., and without drying, and similar measurements were made on the respective products, with the results being shown in Table 2.

started 24 hours after the transplantation. In the case of intra-peritoneal administration, the substance was administered in a dose of 10 mg/kg once a day and every other day for the period of 20 days to give a total amount of 0.2 ml/20 gr (mouse body weight), and in the case of oral administration, the substance was given at a dose of 1000 mg/kg once a day continuously for the period of 20 days to give a total amount of 0.2 ml/20 gr (mouse body weight). Each tumour was enucleated 25 days after the transplantation, and the tumour inhibition Table 2

| Specimen No. | Examples | | | | | Comparative Examples | | |
|---|---|---|---|---|---|---|---|---|
| | 1 | 2 | 3 | 4 | 5 | 1 | 2 | 3 |
| Drying temperature (°C) | 65 | 80 | 90 | 110 | 145 | 45 | 160 | No drying |
| Water content (wt.%) after drying treatment | 20 | 20 | 17 | 12 | 6 | 50 | 2 | — |
| Amount of dried culture (kg) | 31 | 31 | 30 | 28 | 27 | 50 | 26 | — |
| Amount of hot water used for extraction (l) | 250 | 250 | 250 | 250 | 250 | 350 | 250 | 0 |
| Apparent viscosity (cps) of mixture system used in extraction | 150 | 150 | 100 | 100 | 100 | 200 | 100 | 250 |
| Time (min) required for separation | 35 | 35 | 35 | 30 | 30 | 60 | 30 | 90 |
| Time (hr) required for ultrafiltration | 5.5 | 5.5 | 5.5 | 5 | 5 | 10 | 5 | 20 |
| Critical concentration (wt%) of refined solution | 15 | 15 | 15 | 15 | 15 | 8 | 15 | 4 |
| Time (hr) required for spray drying | 10 | 10 | 10 | 10 | 10 | 24 | 10 | 37 |
| Yield (g) | 900 | 900 | 900 | 900 | 900 | 950 | 800 | 950 |
| Anti-tumor activities (tumor inhibition (%)): | | | | | | | | |
| Intra-peritoneal administration | 96 | 97 | 95 | 98 | 97 | 93 | 60 | 95 |
| Oral adminstration | 65 | 67 | 70 | 60 | 62 | 65 | 10 | 71 |
| Remarks | | | | | | contained impurities | contained impurities | |

It is understood from the numerical values given in Table 2 above that when the culture obtained from the process of this invention is subjected to a drying treatment under the specified temperature condition, particularly at a temperature within the range of 60 to 150° C., the ensuing extraction treatment, the extract refining treatment and the refined solution concentrating and spray-drying treatment can be accomplished very advantageously.

Each of the thus obtained polysaccharide products was a brown powder easily soluble in water. (The product of Comparative Example 3 contained a trace amount of insolubles). The results of the elemental analysis of the products showed that each product was composed of C, H, N and O, of which N accounted for about 3 to 3.5 %. Also, the results of the various color reaction tests shown in Table 1 indicated the nature of the products. It was confirmed from these results that the products mentioned above were nitrogen-containing polysaccharides.

The inhibitory activities of the polysaccharides against Sarcoma-180 solid tumours in mice upon both intraperitoneal and oral administrations were as shown in Table 2, indicating the excellent inhibitory activities in all cases except when the drying treatment was performed at a high temperature exceeding 150° C.

The tumor inhibitory effect was measured according to an ordinary employed method which is briefly described below.

The Sarcoma-180 tumour cells were transplanted intraperitoneally into a first control group of mice and, after 7-days growth, $10^6$ of these cells were transplanted under the skin of the other mice to form solid tumours. Administration of the polysaccharide specimens was started 24 hours after the transplantation. ratio was calculated from the average weight of tumours in the groups of mice to which the substance was administered and the average weight of tumours in the control group.

What is claimed is:

1. In a method of producing a nitrogen-containing polysaccharide by cultivating a fungus belonging to the genus Coriolus in an aqueous culture medium by sumberged cultivation, drying the thus cultivated mycelia, extracting the thus obtained dried substance with water or an aqueous alkaline solution and, treating the thus obtained extract by ultrafiltration or reverse osmosis to remove substances having a molecular weight of less than 5,000, the improvement comprising:

drying said cultivated mycelia together with the culture medium without separating the mycelia and the culture medium from each other at a temperature of 60-150° C. to reduce the moisture content of the dried substance to less than 20% by weight.

2. The method according to claim 1, wherein said extraction with an aqueous solvent is carried out in multiple stages.

3. The method according to claim 2, wherein said aqueous solvent is a dilute alkaline solution.

4. The method according to claim 1, wherein said refining of the extract solution is carried out by ultrafiltration.

5. The method of claim 1 in which said fungus of genus Coriolus is selected from the group consisting of Coriolus versicolor (Fr.) Quel, Coriolus consors (Berk.) Imaz., Coriolus hirsutus (Fr.) Quel, Coriolus pargamenus (Fr.) Pat., Coriolus pubescens (Fr.) Quel and Coriolus conchifer (Schw.) Pat.

* * * * *